(12) United States Patent
Clifford et al.

(10) Patent No.: US 9,486,319 B2
(45) Date of Patent: Nov. 8, 2016

(54) LOAD TRANSFERRING SYSTEMS

(71) Applicant: Moximed, Inc., Hayward, CA (US)

(72) Inventors: Anton G. Clifford, Mountain View, CA (US); Andrew H. Jones, San Jose, CA (US); Imraan Aziz, Oakland, CA (US); Clinton N. Slone, San Francisco, CA (US); Thomas King, Redwood City, CA (US); Michael Strasser, San Francisco, CA (US); Des Regan, Co Galway (IE)

(73) Assignee: MOXIMED, INC., Hayward, CA (US)

( * ) Notice: Subject to any disclaimer, the term of this patent is extended or adjusted under 35 U.S.C. 154(b) by 186 days.

(21) Appl. No.: 13/894,261

(22) Filed: May 14, 2013

(65) Prior Publication Data
US 2013/0325123 A1    Dec. 5, 2013

Related U.S. Application Data

(60) Provisional application No. 61/646,738, filed on May 14, 2012.

(51) Int. Cl.
*A61F 2/38*    (2006.01)
*A61B 17/56*    (2006.01)

(52) U.S. Cl.
CPC ............. *A61F 2/38* (2013.01); *A61B 17/56* (2013.01); *A61B 2017/567* (2013.01)

(58) Field of Classification Search
USPC ........... 623/17.11–17.13, 18.11, 20.14–20.28
See application file for complete search history.

(56) References Cited

U.S. PATENT DOCUMENTS

| | | | |
|---|---|---|---|
| 6,022,377 A | 2/2000 | Nuelle et al. | |
| 2006/0064169 A1 | 3/2006 | Ferree | |
| 2008/0275555 A1 | 11/2008 | Makower et al. | |
| 2008/0275567 A1* | 11/2008 | Makower et al. | 623/23.41 |
| 2010/0114322 A1 | 5/2010 | Clifford et al. | |
| 2011/0093079 A1 | 4/2011 | Slone et al. | |
| 2011/0282255 A1* | 11/2011 | Nace | 602/16 |

FOREIGN PATENT DOCUMENTS

EP    0903125    3/1999

OTHER PUBLICATIONS

Supplementary European Search Report for European Patent App. No. 13790530 (Jan. 20, 2016).

* cited by examiner

*Primary Examiner* — Yashita Sharma
(74) *Attorney, Agent, or Firm* — Cermak Nakajima & McGowan LLP; Adam J. Cermak

(57) ABSTRACT

Load transferring systems and related methods for transferring load in a joint are provided. The load transferring system may include two bases configured to couple to bones defining a joint and a spring configured to couple to the bases. The spring may be configured to exert a tensile force between the bases during flexion of the joint. The load transferring system may be employed to treat symptoms associated with osteoarthritis of the lateral compartment of the knee joint. Thus, the bases may respectively couple to the femur and tibia. The spring may exert tensile force therebetween during flexion of the knee joint so as to unload the lateral compartment of the knee joint by transferring load from the lateral compartment of the knee joint to the medial compartment of the knee joint.

22 Claims, 14 Drawing Sheets

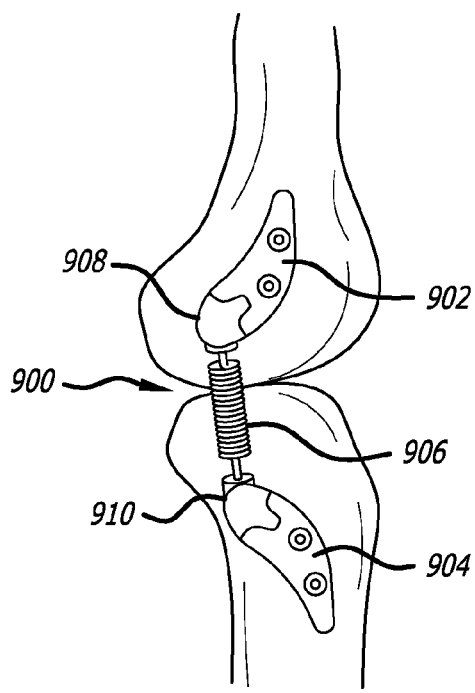 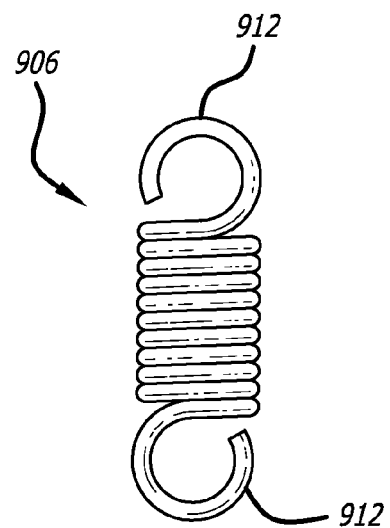
FIG. 12  FIG. 12A
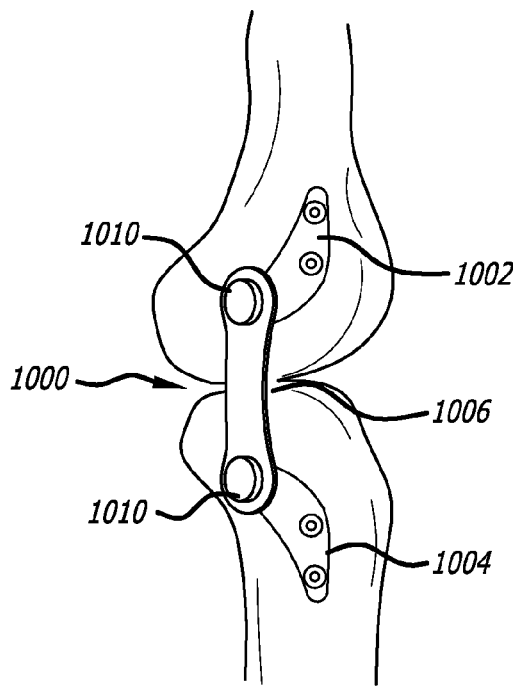 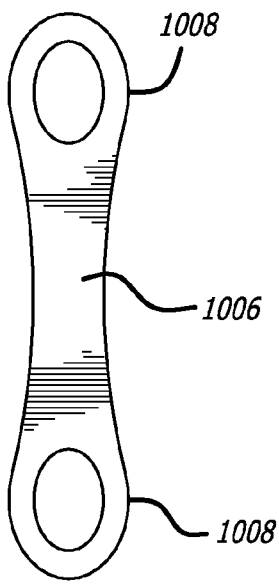
FIG. 13  FIG. 13A

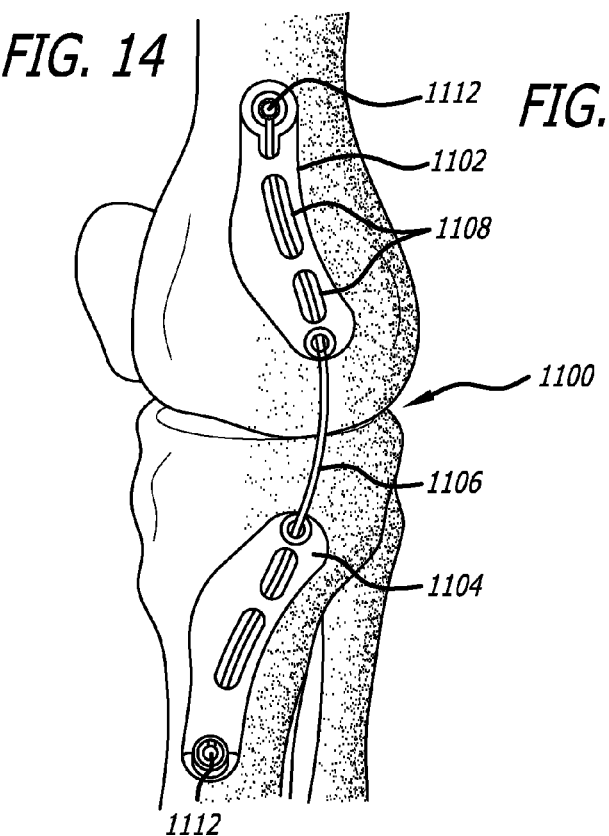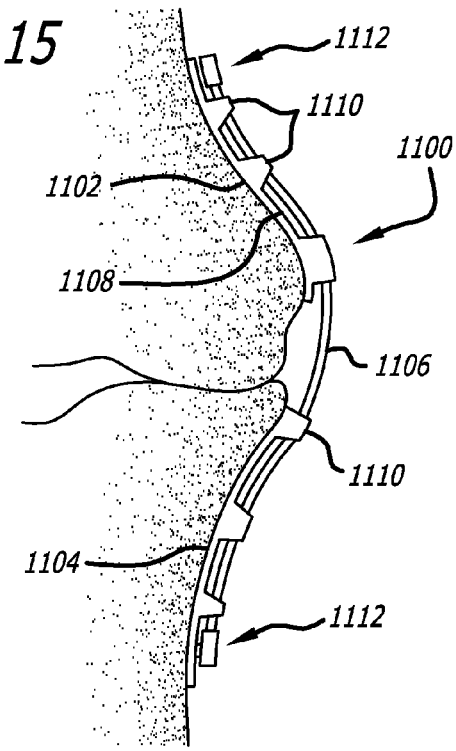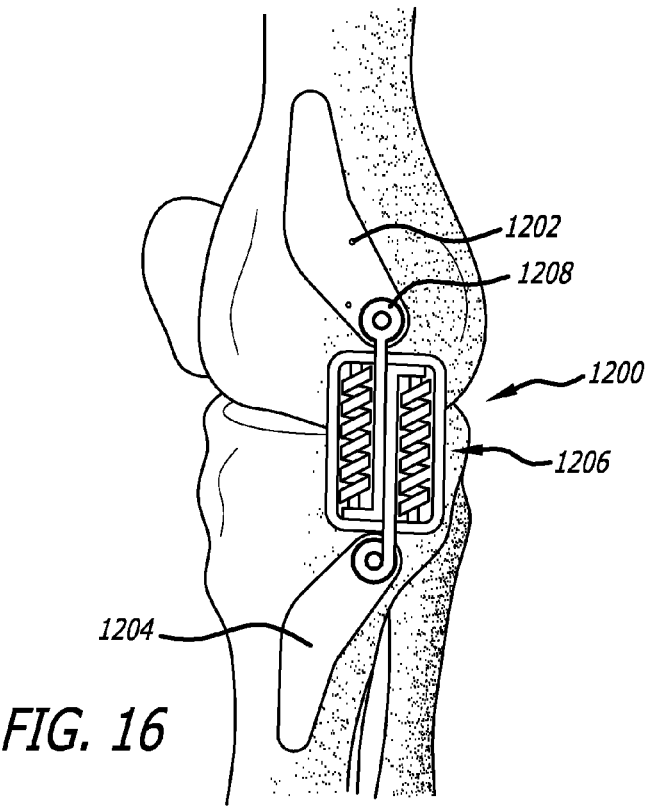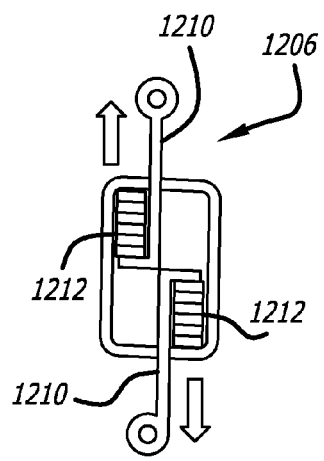
FIG. 14
FIG. 15
FIG. 16
FIG. 16A

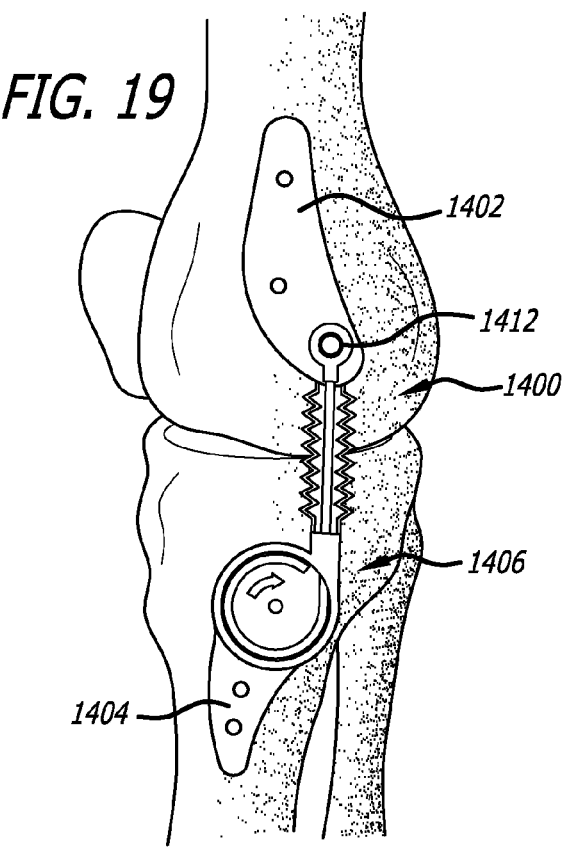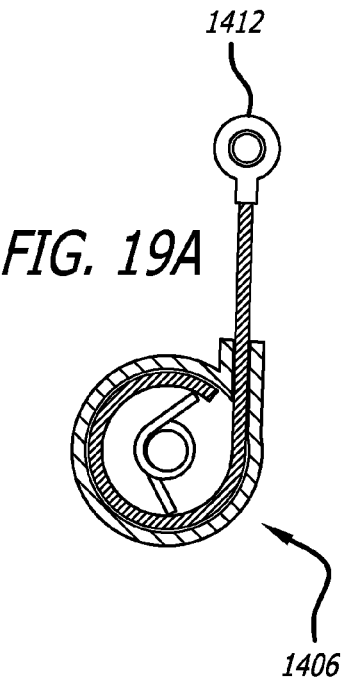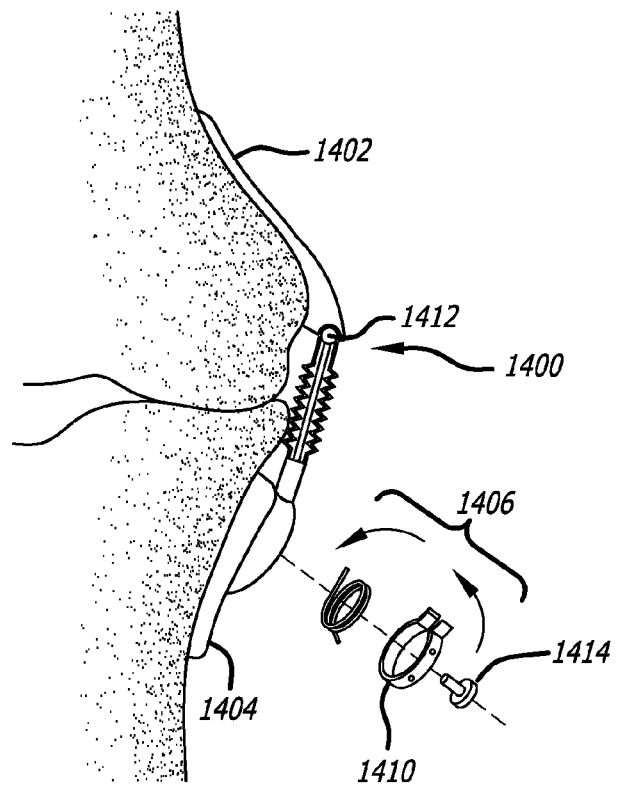

LOAD TRANSFERRING SYSTEMS

CROSS REFERENCES TO RELATED APPLICATIONS

This application claims the benefit of U.S. Application Ser. No. 61/646,738, filed May 14, 2012, the entire disclosure of which is expressly incorporated herein.

FIELD OF THE DISCLOSURE

Various embodiments disclosed herein are directed to structures for attachment to body anatomy, and more particularly, towards load transferring systems for attachment to joints and related methods.

BACKGROUND

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such joint replacement procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced.

Arthroplasty, as a general term, is an orthopaedic procedure which surgically alters the natural joint in some way. Arthroplasty includes procedures in which the arthritic or dysfunctional joint surface is replaced with something else as well as procedures which are undertaken to reshape or realigning the joint by osteotomy or some other procedure. A previously popular form of arthroplasty was interpositional arthroplasty in which the joint was surgically altered by insertion of some other tissue like skin, muscle or tendon within the articular space to keep inflammatory surfaces apart. Another less popular arthroplasty is excisional arthroplasty in which articular surfaces are removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity.

The most common arthroplasty procedures including joint replacement, osteotomy procedures and other procedures in which the joint surfaces are modified are highly invasive procedures and are characterized by relatively long recovery times. When it is successful, arthroplasty results in new joint surfaces which serve the same function in the joint as did the surfaces that were removed. Any chodrocytes (cells that control the creation and maintenance of articular joint surfaces), however, are either removed as part of the arthroplasty, or left to contend with the resulting new joint anatomy and injury. Because of this, none of these currently available therapies are chondro-protective.

A widely-applied type of osteotomy is one in which bones beside the joint are surgically cut and realigned to improve alignment in the joint. A misalignment due to injury or disease in a joint related to the direction of load can result in an imbalance of forces and pain in the affected joint. The goal of osteotomy is to surgically re-align the bones at a joint such as by cutting and reattaching part of one of the bones to change the joint alignment. This realignment relieves pain by equalizing forces across the joint. This can also increase the lifespan of the joint. The surgical realignment of the knee joint by high tibial osteotomy (HTO) (the surgical realignment of the upper end of the shin bone (tibia) to address knee misalignment) is an osteotomy procedure done to address osteoarthritis in the knee. When successful, HTO results in a decrease in pain and improved function. However, HTO does not address ligamentous instability—only mechanical alignment. Good early results associated with HTO often deteriorate over time.

Other approaches to treating osteoarthritis involve an analysis of loads which exist at a joint and attempts to correct (generally reduce) these loads. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Osteoarthritis or breakdown of cartilage due to wear and tear can also result from overloading. When cartilage breaks down, the bones rub together and cause further damage and pain. Finally, if the load rises too high, then abrupt failure of bone, cartilage and other tissues can result.

The treatment of osteoarthritis and other bone and cartilage conditions is severely hampered when a surgeon is not able to control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain. However, lack of patient compliance and the inability of the devices to facilitate and support the natural motion and function of the diseased joint have been problems with these external braces.

With the foregoing applications in mind, it has been found to be necessary to develop effective structures for mounting to body anatomy which conform to body anatomy and cooperate with body anatomy to achieve desired load reduction and transfer. The structure should also provide a base for attachment of complementary structure across articulating joints.

SUMMARY OF THE DISCLOSURE

Described herein are load transferring systems and methods for transferring load in a joint. One embodiment of a load transferring system may include two bases configured to couple to bones defining a joint and a force applier, e.g., a spring, configured to couple to the bases. The spring may be configured to exert a tensile force between the bases during flexion of the joint.

In one exemplary embodiment the load transferring system may be employed to treat symptoms related to osteoarthritis of the lateral compartment of the knee joint. The bases may respectively couple to the femur and tibia at medial aspects thereof. The spring may exert tensile force between the bases during flexion of the knee joint so as to unload the lateral compartment of the knee joint by transferring load from the lateral compartment of the knee joint to the medial compartment of the knee joint.

BRIEF DESCRIPTION OF THE DRAWINGS

The drawings are exemplary only, are not necessarily drawn to scale, and should not be construed as limiting the disclosure.

FIG. 12 is a perspective view of a load transferring system using a coil tension spring;

FIG. 12A is a side view of the coil spring of FIG. 12;

FIG. 13 is a perspective view of a load transferring system using an elastomeric strip spring element;

FIG. 13A is a side view of the elastomeric strip of FIG. 13;

FIG. 14 is a perspective view of a load transferring system using low profile bases and an elongated elastomeric band;

FIG. 15 is a posterior perspective view of the system of FIG. 14;

FIG. 16 is a schematic cut away perspective view of a load transferring system with a double spring;

FIG. 16A is a cross sectional view of the double spring element of FIG. 16;

FIG. 19 is a perspective view of a load transferring system with a torsion spring tensioner;

FIG. 19A is a schematic view of the tensioner of FIG. 19;

FIG. 20 is a posterior exploded view of the load transferring system of FIG. 19;

DETAILED DESCRIPTION OF THE PREFERRED EMBODIMENTS

The present disclosure now will be described more fully hereinafter with reference to the accompanying drawings. The disclosure may be embodied in many different forms and should not be construed as limited to the embodiments set forth herein; rather, these embodiments are provided so that this disclosure will satisfy applicable legal requirements. Like numbers refer to like segments throughout. As used in this specification and the claims, the singular forms "a," "an," and "the" include plural references unless the context clearly dictates otherwise.

As described herein, embodiments of the disclosure relate to load transferring systems for a joint, and related methods. In one exemplary embodiment, the load transferring systems and methods are configured to address osteoarthritis of the lateral compartment of a knee joint. However, it should be understood that the systems and method described herein may be employed with other joints and maladies associated therewith.

Figure 1:
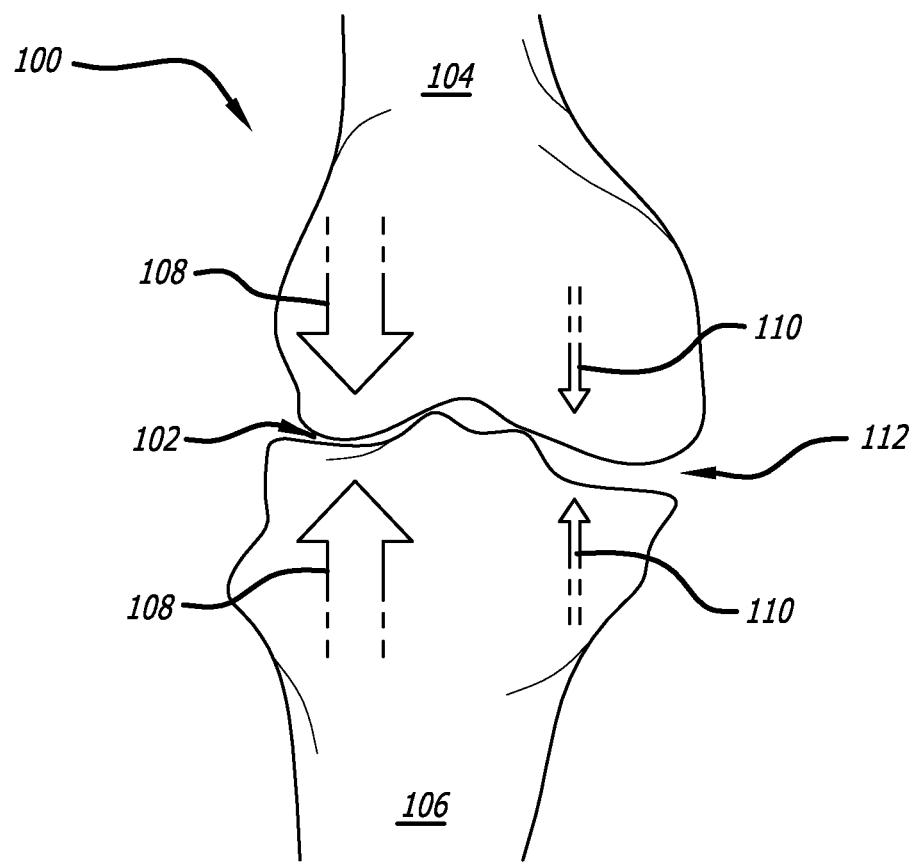
FIG. 1 is a front x-ray view of a right knee joint schematically illustrating uneven loads on a medial compartment and a lateral compartment thereof.

Osteoarthritis of the lateral compartment of the knee joint differs from osteoarthritis of the medial compartment in a number of aspects. For example, whereas osteoarthritis of the medial compartment tends to cause pain during knee extension, osteoarthritis of the lateral compartment tends to cause pain during knee flexion. In this regard, FIG. 1 illustrates a view though a right knee joint 100 experiencing osteoarthritis of the lateral compartment 102 between the femur 104 and the tibia 106. As schematically illustrated, pain associated with osteoarthritis of the lateral compartment 102 may result from an imbalance of a load 108 on the lateral compartment of the knee joint 100 as compared to a load 110 on the medial compartment 112 of the knee joint causing wear and deterioration of the cartilage on the lateral side of the joint.

Accordingly, pain associated with osteoarthritis of the lateral compartment may be addressed by reducing load on the lateral compartment of the knee joint. In order to address issues associated with osteoarthritis of the medial compartment, Applicants have previously designed apparatuses and systems for transferring load from the medial compartment through an absorber mounted to femoral and tibial bases on the medial aspects thereof. The absorber for treatment of medial knee osteoarthritis transfers load from the medial compartment of the knee joint by acting in compression during extension of the knee joint.

Figure 2:
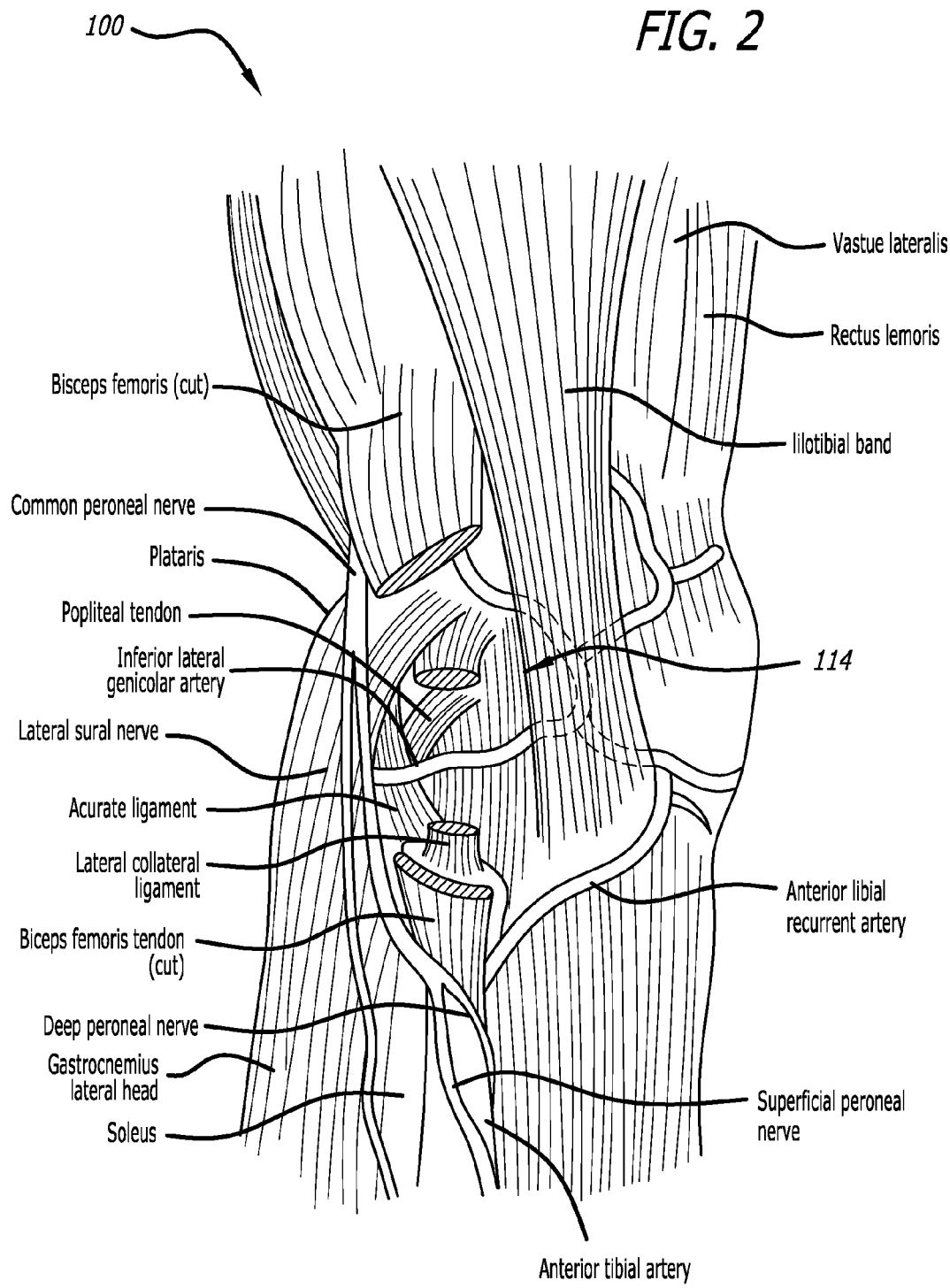
FIG. 2 is a side view of the components of a right knee joint at a lateral aspect thereof.
Figure 3:
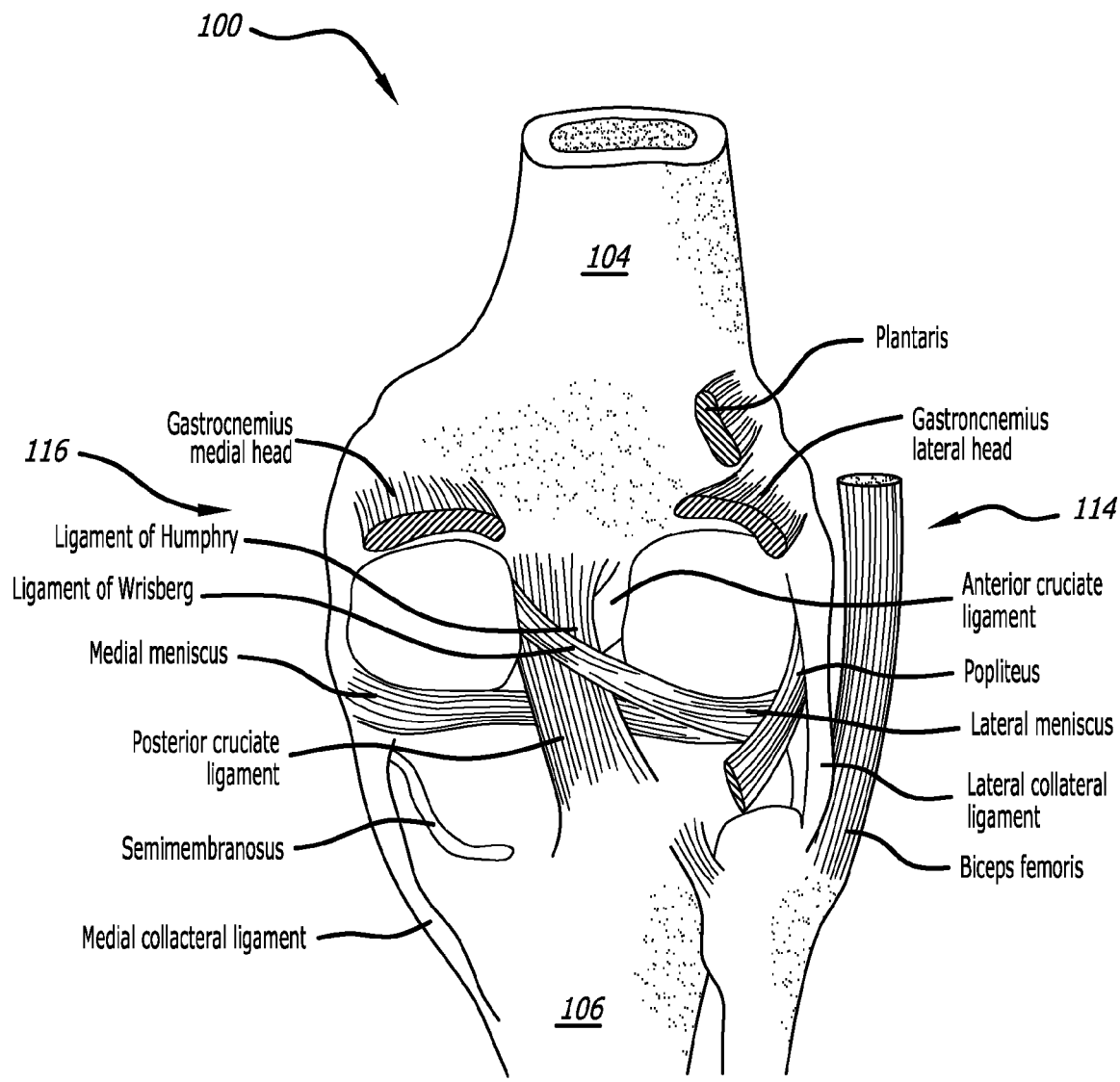
FIG. 3 is a front view of a left knee joint with components thereof removed to illustrate a femur bone and a tibia bone.

As illustrated in FIG. 2, the lateral aspect 114 of the knee joint 100 defines a complex structure of musculoskeletal, vascular, and neurological structures. As a result of this complex anatomy, suitable attachment points for femoral and tibial bases may not be available on the lateral aspect of the knee joint. In comparison, as illustrated in FIG. 3, the medial aspect 116 of the knee joint 100 defines a less complex structure, relative to the lateral aspect 114, which may be more suitable for easily mounting femoral and tibial bases. Further, the lateral compartment 114 of the knee joint 100 is capable of a relatively greater degree of movement than the medial aspect 116 of the knee joint. More particularly, a center of rotation of the lateral compartment of the knee joint moves during flexion by an average of approximately 10 mm. This is compared to the medial compartment where the center of rotation moves only about 1-2 mm between 0 degrees and 90 degrees of flexion. Thus, the medial aspect 116 of the knee joint 110 may also be favorable as compared to the lateral aspect 114 of the knee joint, in terms of a location for attachment of a device, due to the medial aspect of the joint being subjected to a lesser degree of movement. Accordingly, it may be preferable to attach a device to the medial aspect 116 of the knee joint 110 due to its relatively simpler structure and reduced kinematic requirements.

Figure 4:
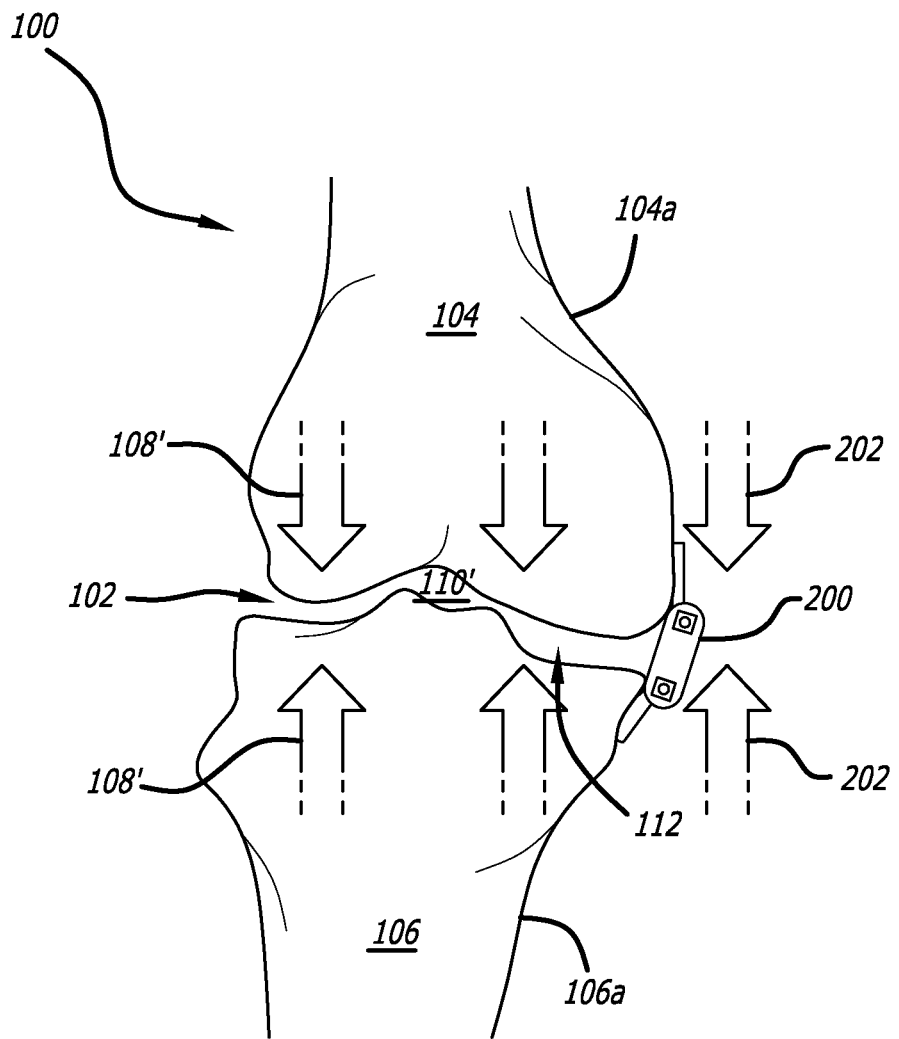
FIG. 4 is a front x-ray view of a right knee joint schematically illustrating a device employed to balance the loads on the medial compartment and the lateral compartment according to an example embodiment of the present disclosure.

In order to address issues associated with osteoarthritis of the lateral compartment, as opposed to the medial compartment, a device must address the above noted requirements. Accordingly, as schematically illustrated in FIG. 4, Applicants herein provide a device 200 configured to transfer loads in the knee joint 100 so as to mitigate effects associated with osteoarthritis of the lateral compartment 102 of the knee joint 100. In particular, the device 200 is configured to exert a tensile force 202 between the femur 104 and the tibia 106 at lateral aspects 104a, 106a thereof during flexion of the knee joint 100. Thereby, the load 108' on the lateral compartment 102 of the knee joint 100 may be reduced and the load 110' on the medial compartment 112 may be increased in order to balance the loads during flexion. In addition to providing unloading of the lateral compartment 102 of the knee joint 100, the device 200 provides resistance to valgus movements of the knee joint, particularly resistance to valgus movements of the joint in flexion.

Figure 5:
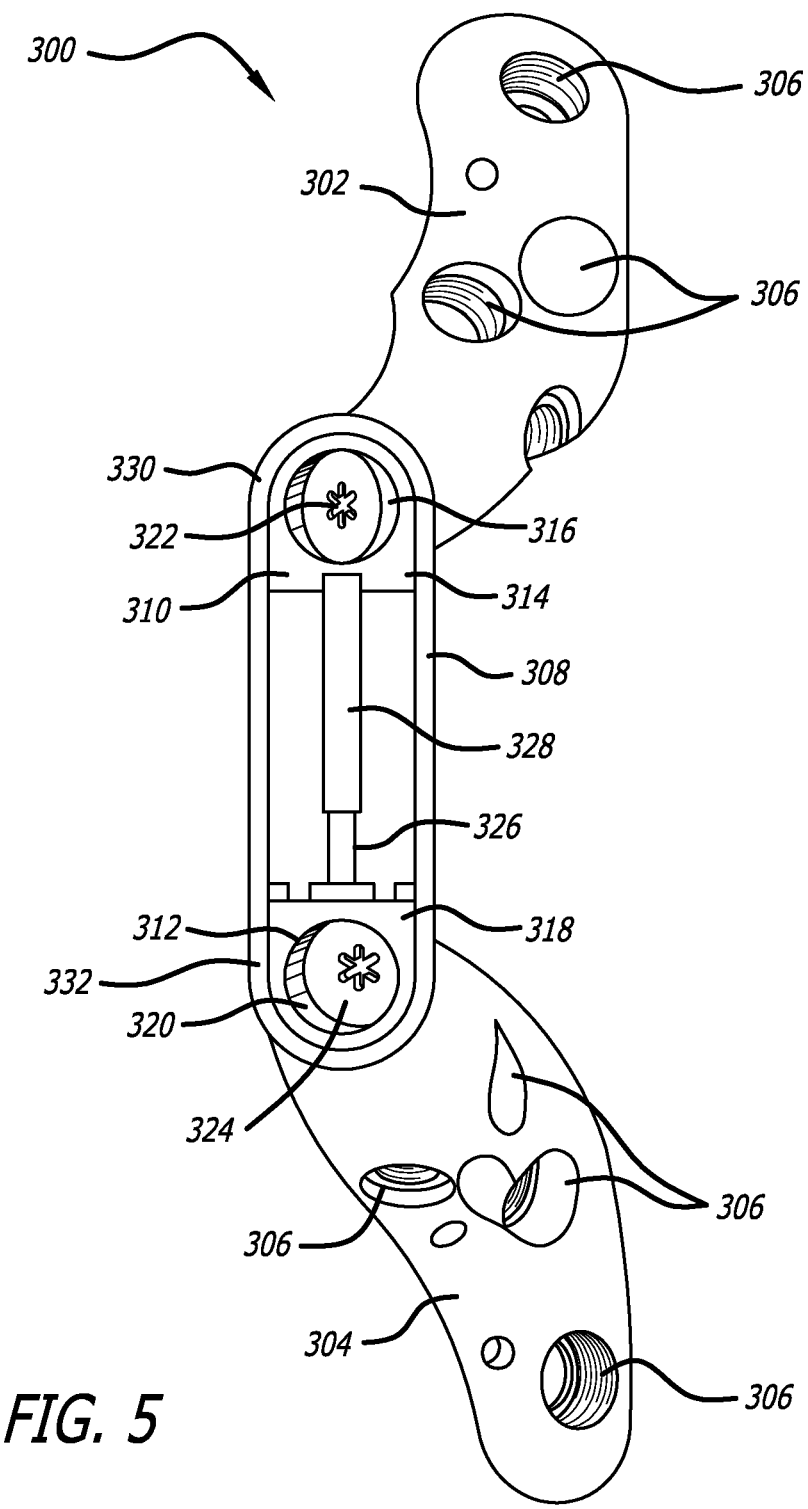
FIG. 5 is a front view of a load transferring system for a left knee joint according to a first example embodiment of the present disclosure.

In one embodiment, the device 200 schematically illustrated in FIG. 4 may be embodied as a load transferring system. In this regard, FIG. 5 illustrates an example embodiment of a load transferring system 300 according to the present disclosure. The load transferring system 300 includes a first (femoral) base 302 configured for implantation and coupling to a medial aspect of a femur. The load transferring system 300 also includes a second (tibial) base 304 configured for implantation and coupling to a medial aspect of a tibia. In one embodiment the femoral and tibial bases 302, 304 may be the same as, or similar to, the femoral and tibial bases disclosed in U.S. Patent Application Publication No. 2011/0245928 to Landry et al., which is incorporated herein by reference in its entirety. However, various other embodiments of the femoral and tibial bases 302, 304 may be employed.

The femoral and tibial bases 302, 304 may be configured to define a low profile and match the shape of the femur and the tibia, respectively. Matching the shape of the medial aspects of the femur and the tibia may allow the femoral and tibial bases 302, 304 to evenly distribute loads applied thereto. Further, by defining a low profile, the femoral and tibial bases 302, 304 may enable substantially atraumatic movement of the adjacent soft tissue thereagainst.

One or more apertures 306 may be defined in the femoral and tibial bases 302, 304. The apertures 306 may be configured to receive a fastener so as to respectively secure the femoral and tibial bases 302, 304 to the femur and the tibia. In some embodiments the apertures 306 may be divergent so as to provide for multi-axial compression of the femoral and tibial bases 302, 304 against the femur and tibia. Additionally, the apertures 306 may be threaded so as to engage threads of fasteners.

The load transferring system 300 may further comprise spring means 308 configured to be connected to the femoral base 302 and the tibial base 304. Spring means 308 is configured to exert a tensile force between the femoral base 302 and the tibial base 304 during flexion of the knee joint. Thereby, the load transferring system 300 may unload the lateral compartment of the knee by transferring load from the lateral compartment of the knee joint to a medial compartment of the knee joint.

Spring means 308 may be configured to substantially avoid exerting tensile force on the knee joint when the knee joint is in a fully extended position. In this regard, osteoarthritis of the lateral compartment of the knee joint most commonly causes pain in flexion, rather than extension. Spring means 308 may also be configured to completely or substantially avoid transferring a force between the femoral base 302 and the tibial base 304 in compression. Transferring force between the femoral base 302 and the tibial base 304 under compression may be undesirable because this may transfer additional load to the lateral compartment of the knee joint.

In some embodiments spring means 308 may comprise an elastomeric band, as illustrated. The elastomeric band may be configured to substantially avoid transferring a force between the femoral base 302 and the tibial base 304 under compression because the elastomeric band would fold or bend if exposed to a compressive force. Further, the size (e.g., the length) of the elastomeric band may be selected such that the elastomeric band may define an unbiased configuration, wherein the elastomeric band is neither stretched nor compressed, when the knee joint is in a fully extended configuration. Thereby, the elastomeric band may also avoid exerting tensile force on the knee joint when the knee joint is in a fully extended position.

However, spring means 308 may comprise various other types of springs in other embodiments. For example, spring means 308 may comprise a wire spring, such as a coil spring. The length of the wire spring may be selected such that the wire spring may define an unbiased configuration, wherein the wire spring is neither stretched nor compressed, when the knee joint is in a fully extended configuration. Thereby, the wire spring may avoid exerting tensile force on the knee joint when the knee joint is in a fully extended position. Further the wire spring may avoid transferring a force between the femoral base 302 and the tibial base 304 under compression because the unbiased position of the wire spring may correspond with the fully extended position of the knee joint such that the wire spring is not subjected to compression.

In some embodiments the load transferring system may additionally include a first connector means 310 configured to engage the femoral base 302 and spring means 308 and a second connector means 312 configured to engage the tibial base 304 and the spring means. The first connector means 310 may comprise a first articulating member 314 and a first stationary member 316 about which the first articulating member is configured to articulate. Similarly, the second connector means 312 may comprise a second articulating member 318 and a second stationary member 320 about which the second articulating member is configured to articulate. The stationary member 320 and the articulating member 318 as shown form the ball and socket, respectively, of a ball and socket joint allowing articulation in three dimensions. However, the first and second connector means 310, 312 may comprise various other embodiments of connectors, clasps, and structures configured to engage a base and a bone and, in some embodiments, provide for articulation in one or more directions.

The first connector means 310 may include a first fastener means 322 configured to fasten the first stationary member 316 to the femoral base 302, and the second connector means 312 may include a second fastener means 324 configured to fasten the second stationary member 320 to the tibial base 304. The fastener means 322, 324 may comprise a screw, pin, bolt, or various other embodiments of fasteners configured to fasten the stationary members 316, 320 to the bases 302, 304. Accordingly, the fastener means 322, 324 may secure the first and second stationary members 316, 320 such that they are stationary relative to the femoral and tibial bases 302, 304.

A piston 326 may be coupled to one of the first articulating member 314 and the second articulating member 318 and a cylinder 328 may be coupled to the other of the first articulating member and the second articulating member. In the illustrated embodiment the cylinder 328 is coupled to the first articulating member 310 and the piston 326 is coupled to the second articulating member, but the opposite configuration may be employed in other embodiments. The cylinder 328 is configured to receive the piston 326 therein and allow for relative movement therebetween. Thus, as the femoral base 302 and the tibial base 304 move relative to one another during extension and flexion of the knee joint, the piston 326 may move longitudinally inside the cylinder 328. Articulation of the first and second articulating members 314, 318 respectively about the first and second stationary members 316, 320 may allow the piston 326 and the cylinder 328 to remain aligned during movement of the knee joint such that longitudinal movement therebetween is possible. Further, in some embodiments the piston 326 and the cylinder 328 may be configured to allow for rotational movement therebetween. For example, the piston 326 may define a circular cross-section and the cylinder 328 may define a cavity with a circular cross-section perpendicular to the longitudinal axes thereof such that the piston and the cylinder may rotate relative to one another. Accordingly, the load transferring system 300 may substantially avoid restricting movement of the knee joint.

The first and second connector means 310, 312 may include features configured to assist in engaging spring means 308. In the illustrated embodiment, in which spring means 308 is an elastomeric band, the first and second connector means 310, 312 each respectively define a channel 330, 332 configured to receive the spring means. The channels 330, 332 may be sized and shaped such that spring means 308 is retained therein via interference fit in some embodiments. Further, the piston 326 and the cylinder 328 may function to maintain the channels 330, 332 such that they are coplanar, and thereby issues with respect to spring means 308 pulling out of the channels as a result of misalignment therebetween may be avoided.

Figure 6:
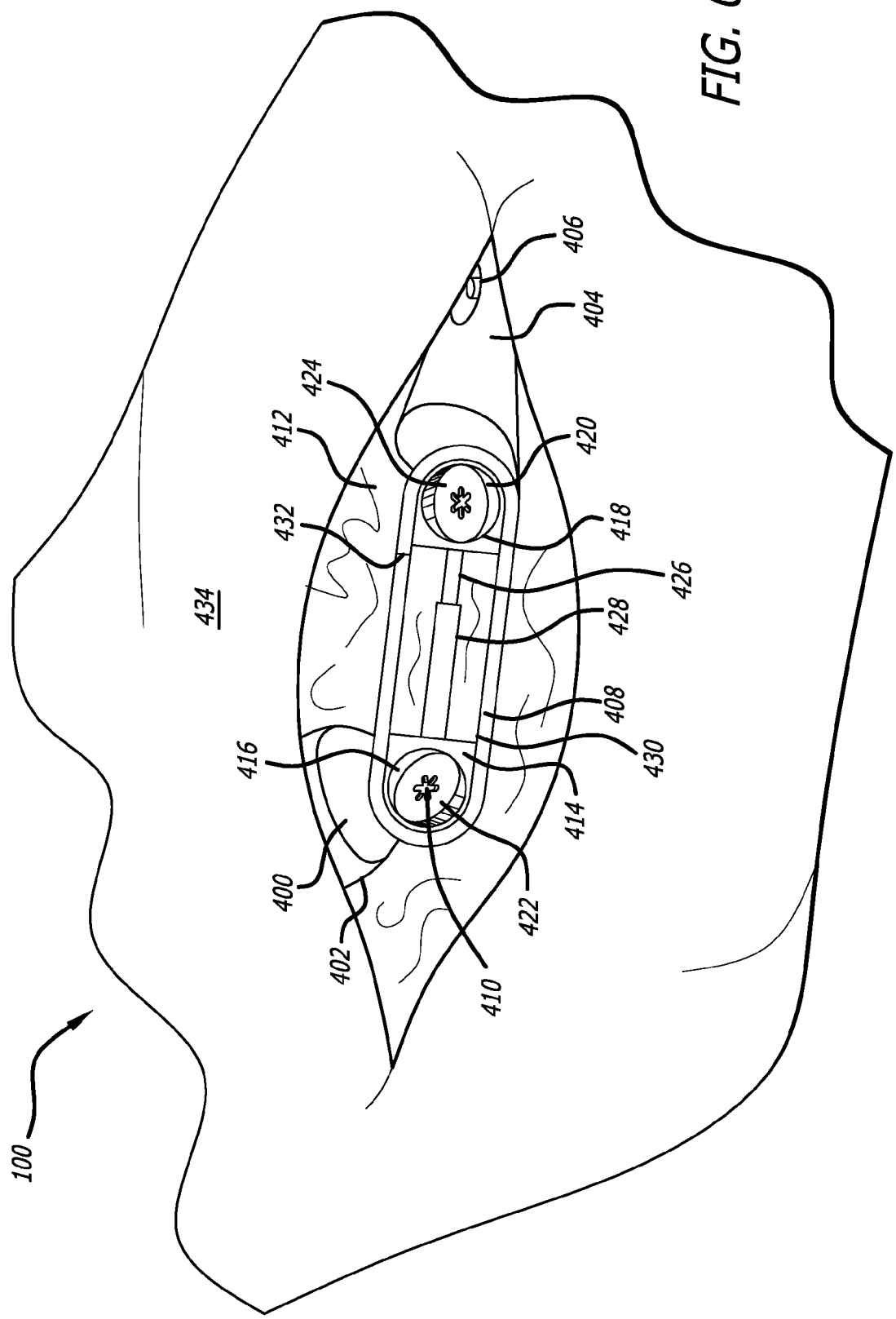
FIG. 6 is a perspective view of a surgically opened left knee joint in which a load transferring system is implanted according to a second example embodiment of the present disclosure.

FIG. 6 illustrates a knee joint 100 which has been surgically opened and to which an embodiment of a load transferring system 400 is attached. The load transferring system 400 is substantially similar to the load transferring system 300 illustrated in FIG. 5, with the exception of the particular shape of the femoral and tibial bases 402, 404 and the number and location of apertures 406 therein. Similar elements are referenced by similar reference numbers.

The load transferring system 400 may be configured such that the femoral and tibial bases 402, 404 slot between surrounding tissue and respectively engage the femur and tibia, which are not visible in FIG. 6 due to surrounding tissue and knee components. Further, as illustrated, the load transferring system 400 mates with the knee joint 100 such that the load transferring system is positioned outside of a joint capsule 434. Accordingly, issues with respect to interfering with the load bearing surfaces of the knee joint 100 may be avoided.

Figure 7:
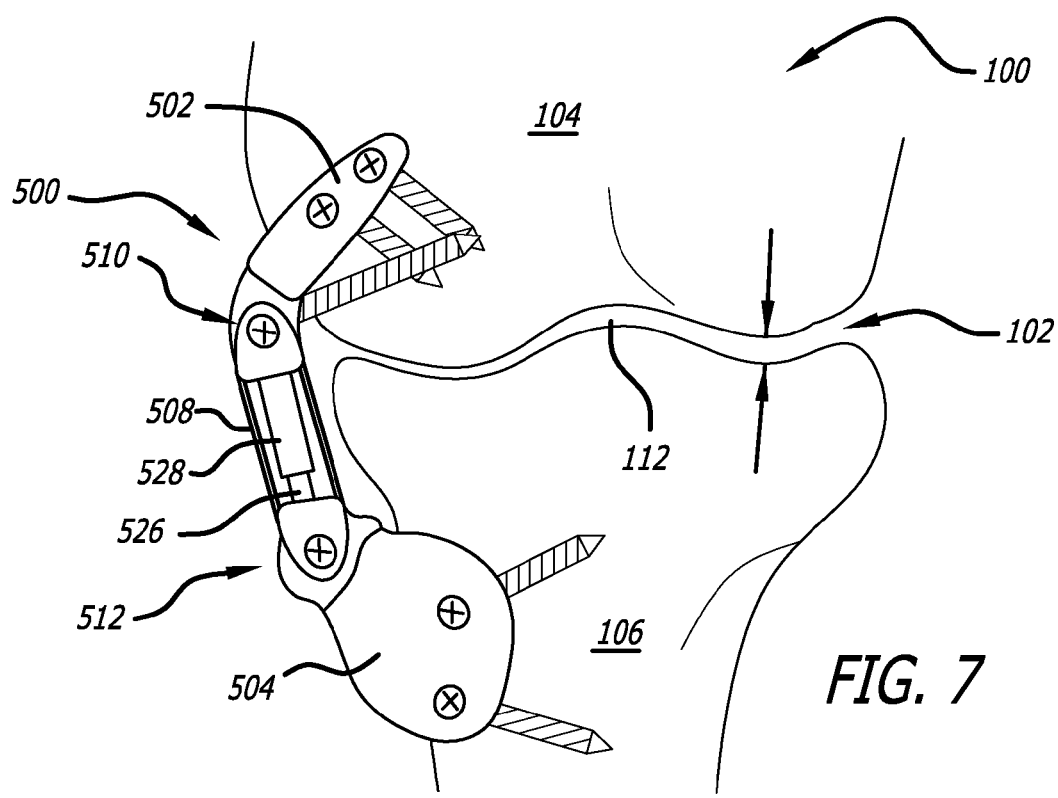
FIG. 7 is a front x-ray view of a left knee joint in an extended position to which a load transferring system is coupled according to a third example embodiment of the present disclosure.
Figure 8:
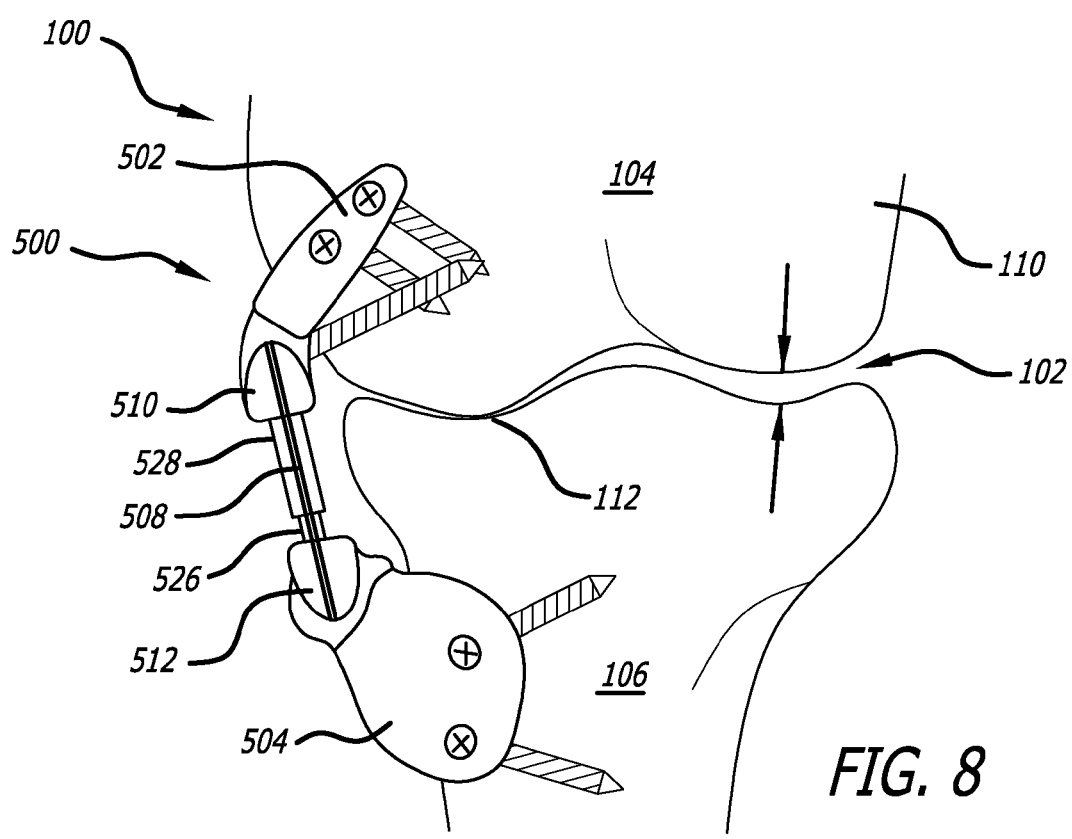
FIG. 8 is a front x-ray view of the left knee joint of FIG. 7 in a flexed position.

FIG. 7 illustrates an x-ray view of a left knee joint 100 to which an embodiment of a load transferring system 500 is attached at the medial side of the joint. The load transferring system 500 may be substantially similar to the embodiments of the load transferring systems 300, 400 discussed above, and hence the features thereof will not be discussed in detail. Specifically, FIG. 7 illustrates the knee joint 100 in an extended configuration. As illustrated, the lateral compartment 102 may be compressed during extension, as a result of the load transferring system 500 substantially avoiding exerting tensile force on the knee joint 100 when the knee joint. However, as the knee joint 100 moves to a flexed position, as illustrated in FIG. 8, the spring means 508 of the load transferring system 500 exerts a tensile force between the femoral base 502 and the tibial base 504 so as to unload the lateral compartment 102 of the knee joint by transferring load from the lateral compartment to the medial compartment 112 of the knee joint. Accordingly, by unloading the lateral compartment 102 of the knee joint 100 during flexion, the load transferring system 500 may reduce symptoms associated with osteoarthritis of the lateral compartment.

The tensile force applied by the load transferring systems described herein can be determined based on the anatomy of the particular knee joint, the patient weight and activity level, and other characteristics. However, in one example, the load transferring system applies a tensile force of approximately 2.5 to 50 pounds at 10 to 90 degrees of flexion and applies substantially no tension or less than 2 pounds of tension when the knee joint is in full extension (zero degrees flexion). Elastomeric bands may be provided in differing lengths and differing thicknesses to allow the surgeon to accurately tailor the tension force to the particular knee joint being treated. In one method of selecting the elastomeric band, the femoral and tibial bases are implanted onto the bone and a tension gauge of known rate is placed across the bases while the knee joint is moved through a predetermined range of motion. A maximum force measured by the tension gauge may be used to select the tension force needed for the tension band or other spring member. In one embodiment, the spring is adjustable to exert the selected tension force.

Figure 9:
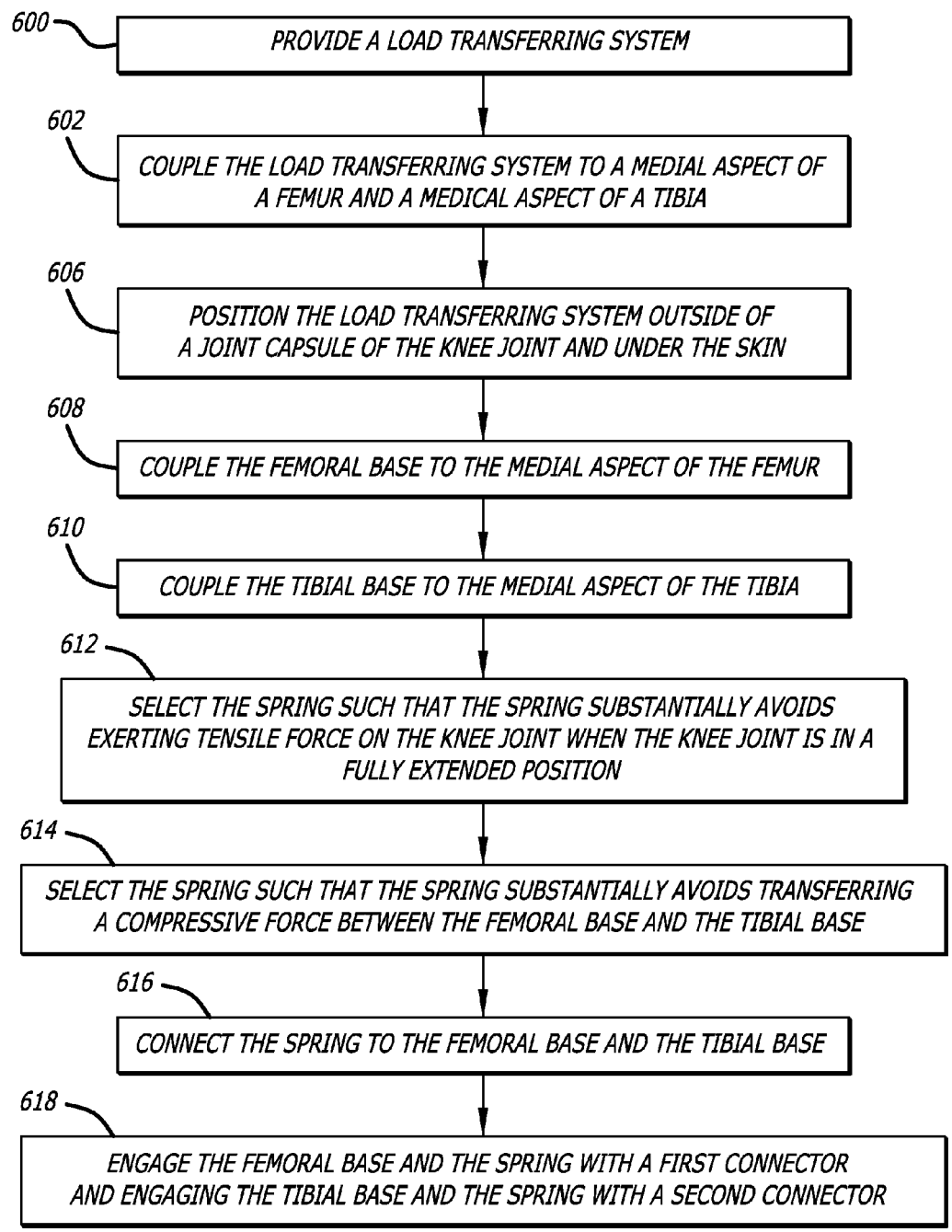
FIG. 9 is a block diagram of a method for transferring load in a knee joint according to an example embodiment of the present disclosure.

FIG. 9 illustrates an embodiment of a related method for transferring load in a knee joint. As illustrated, the method may include providing a load transferring system at operation 600, which may comprise one of the above-described embodiments of load transferring systems in some embodiments. The method may further comprise coupling the load transferring system to a medial aspect of a femur and a medial aspect of a tibia at operation 602. The load transferring system may be configured to exert a tensile force between the medial aspect of the femur and the medial aspect of the tibia during flexion so as to unload a lateral compartment of the knee joint during flexion by transferring load from the lateral compartment of the knee joint to a medial compartment of the knee joint.

In some embodiments coupling the load transferring system to the medial aspect of the femur and the medial aspect of the tibia at operation 602 comprises positioning the load transferring system outside of a joint capsule of the knee joint and under the skin at operation 606. Coupling the load transferring system to the medial aspect of the femur and the medial aspect of the tibia at operation 602 may also include coupling the femoral base to the medial aspect of the femur at operation 608, coupling the tibial base to the medial aspect of the tibia at operation 610, and connecting the spring to the femoral base and the tibial base at operation 616. As illustrated, connecting the spring to the femoral base and the tibial base at operation 616 may be conducted before or after coupling the femoral base to the medial aspect of the femur at operation 608 and coupling the tibial base to the medial aspect of the tibia at operation 610.

Figure 10:
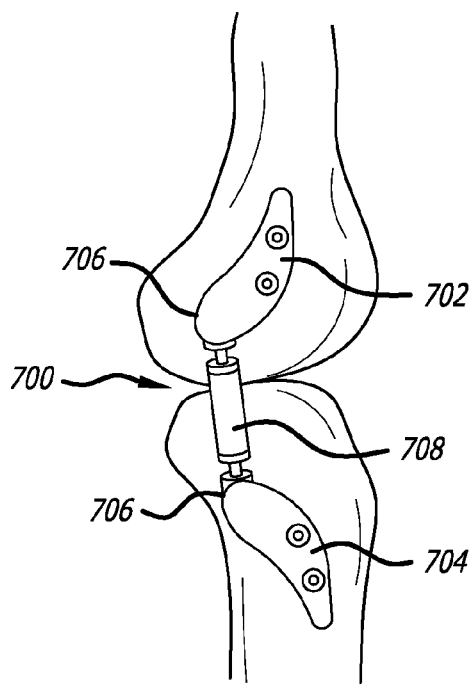
FIG. 10 is a perspective view of a load transferring system using an elastomeric body spring element.
Figure 10A:
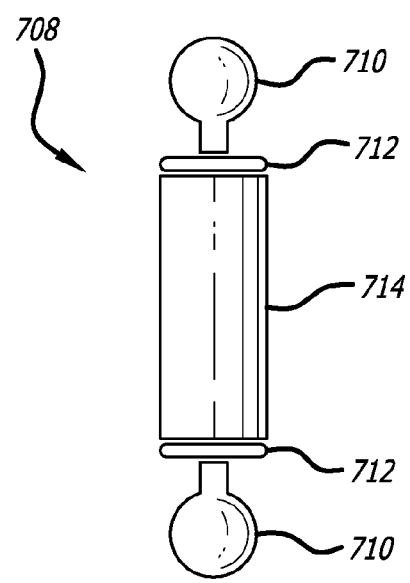
FIG. 10A is a side view of the elastomeric body spring element of FIG. 10.

FIGS. 10 and 10A schematically illustrate a load transferring device 700 which includes a femoral base 702 and a tibial base 704 configured for implantation and coupling to a medial aspect of the knee joint. One or more sockets 706 may be defined in the femoral and tibial bases 702, 704 for receiving a spring element 708. The spring element 708 includes first and second balls 710 received in the sockets 706 of the bases. The spring element 708 includes a cylindrical or other shaped elastomeric or polymer central portion 714 configured to exert a tensile force between the femoral base 702 and the tibial base 704 of the knee joint to unload the medical compartment of the knee joint. Disc shaped metallic caps 712 protect the central polymer portion 714 from contact with the bases. The spring element 708 may be configured to act to unload the medial compartment during flexion, extension or a combination of both flexion and extension.

Figure 11:
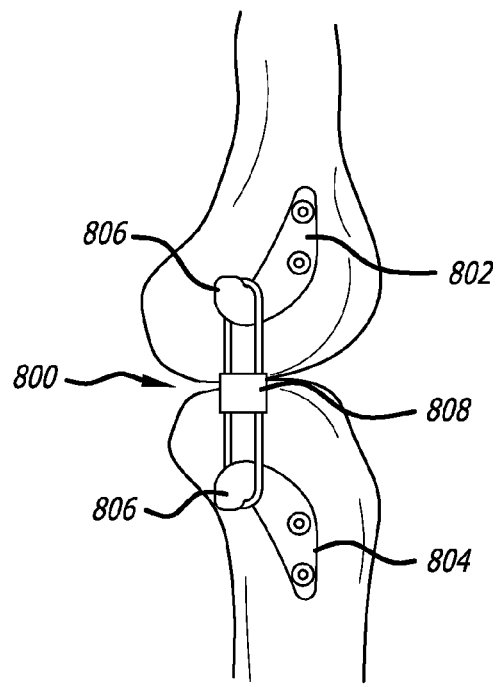
FIG. 11 is a perspective view of a load transferring system using an elastomeric band spring element.
Figure 11A:
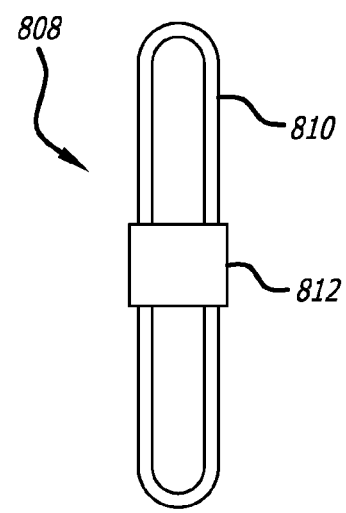
FIG. 11A is a side view of the elastomeric band spring element of FIG. 11.

FIGS. 11 and 11A schematically illustrate a load transferring device 800 which includes a femoral base 802 and a tibial base 804 configured for implantation on the femur and tibia at a medial aspect of the knee joint. One or more hooks 806 may be defined on the femoral and tibial bases 802, 804 for receiving a spring element 808. The spring element 808 includes a polymer or elastomer band 810 optionally secured by a retainer 812. The spring element 808 is received on the hooks 806. The spring element 808 may be configured to act to unload the medial compartment of the joint during flexion, extension or a combination of both flexion and extension.

FIGS. 12 and 12A illustrate a load transferring device 900 which includes a femoral base 902, a tibial base 904, and a spring element 906 configured for implantation and coupling to a medial aspect of the knee joint. The femoral base 902 may include a removable socket 908 while the tibial base may including a removable tibial socket 910. The sockets 908, 910 each include a rod, pin, or other bearing (not shown) for receiving hook or eyelet ends 912. The spring element 908 is configured to act in tension to unload the medial compartment of the joint.

FIGS. 13 and 13B illustrate a load transferring device 1000 similar to that of FIG. 12 in which the tension spring is replaced with a polymer or elastomer tension strip or band 1006. The device 1000 includes a femoral base 1002, a tibial base 1004, and the spring element 1006 configured for implantation and coupling to a medial aspect of the knee joint. The spring element 1006 has openings 1008 at each end to allow the spring element 1006 to be connected to the femoral and tibial bases 1002, 1004 by fasteners 1010. The fasteners 1001 may be screws, bolts, snap lock fasteners, or any other fastener suitable for use in an implant. The tension strip 1006 is configured to act in tension to unload the medial compartment of the joint.

FIGS. 14 and 15 illustrate a load transferring device 1100 which includes a low profile femoral base 1102, a low profile tibial base 1104, and a spring element 1106 in the form of a tension band. The tension band 1106 is positioned beneath a portion of the bases 1102, 1104 and held in place by a plurality of bridges 1110 of the bases. To further reduce the profile of the bases 1102, 1104 the bases are provided with openings 1108. The tension band 1106 is secured by anchors 1112 and is configured to act in tension to unload the medial compartment of the joint. The additional length of the tension band 1106 can allow the use of a less elastic material as the band can absorb forces along its entire length.

FIGS. 16 and 16A schematically illustrate a load transferring device 1200 which includes a femoral base 1202, a tibial base 1204, and a spring element 1206 configured for implantation and coupling to a medial aspect of the knee joint. The femoral and tibial bases 1202, 1204 may each include a socket 1208 or other rotational joint for receiving the spring element 1206 in a manner which allows rotational motion. The spring element 1206 includes two pistons 1210 and corresponding two springs 1212 which act in compression to unload the medial compartment of the joint.

Figure 17:
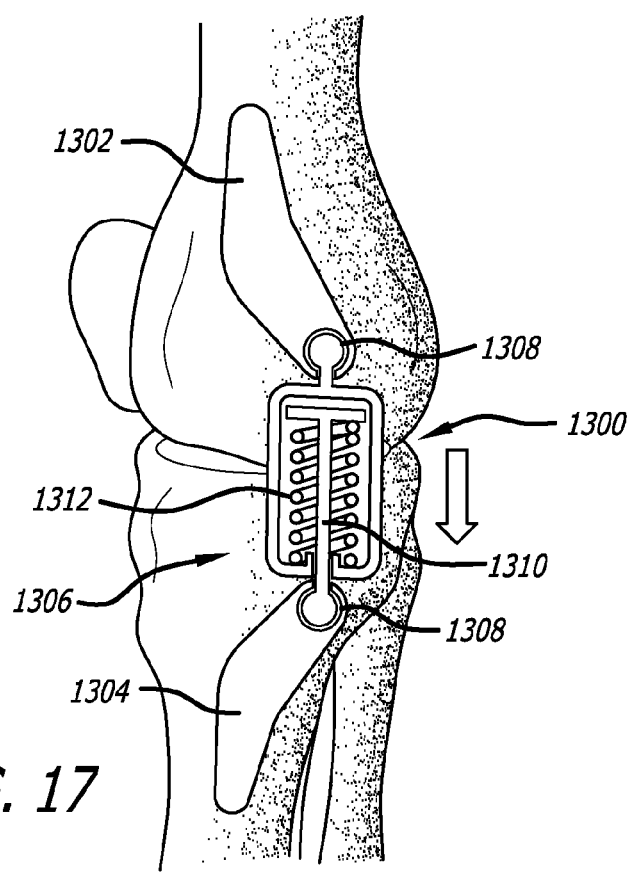
FIG. 17 is a schematic cut away perspective view of a load transferring system with a single spring.
Figure 18:
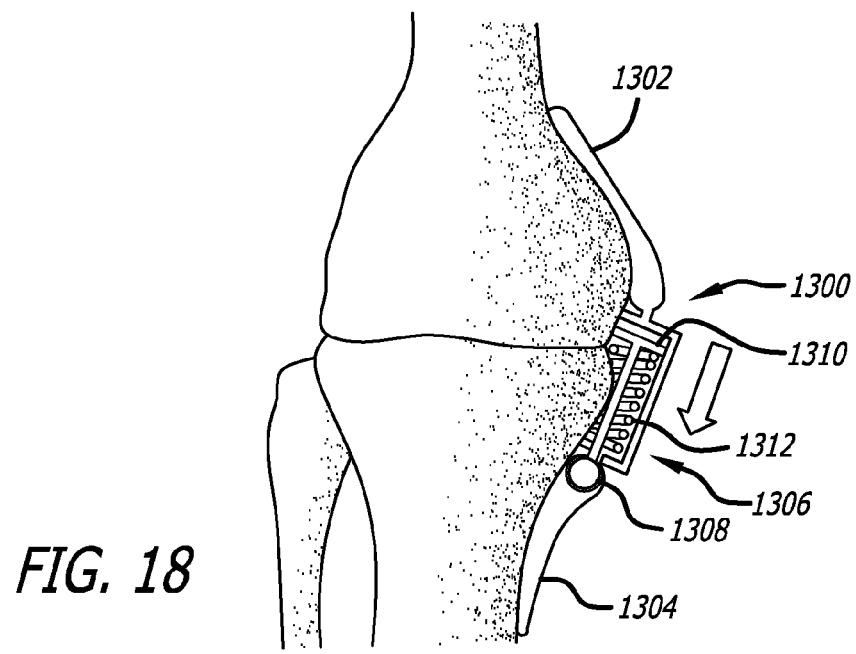
FIG. 18 is a schematic posterior view of the system of FIG. 17.

FIGS. 17 and 18 schematically illustrate a load transferring device 1300 which includes a femoral base 1302, a tibial base 1304, and a spring element 1306 configured for implantation and coupling to a medial aspect of the knee joint. The femoral and tibial bases 1302, 1304 may each include a socket 1308 or other rotational joint for receiving the spring element 1306 as described in further detail with respect to other embodiments described herein. The spring element 1306 includes a piston 1310 and corresponding spring 1312 which act in compression to unload the medial compartment of the joint. Although a laser cut cylindrical coil spring has been shown, other spring configurations can also be used.

FIGS. 19, 19A and 20 schematically illustrate a load transferring device 1400 using a torsion spring element. The device 1400 includes a femoral base 1402, a tibial base 1404, and a spring element 1406 configured for implantation and coupling to a medial aspect of the knee joint. The spring element 1406 is a torsion spring element which is formed as a part of the tibial base 1404. The torsion spring element 1406 includes a wire or cable 1408 connected at one end to a rotating tensioner 1410 and at the other end to a pivoting connection 1412 on the femoral base 1402. Within the rotating tensioner 1410 is torsion spring 1412 which applies a rotational force to the tensioner 1410 and the cable 1408. The rotating tensioner 1410 is held to the tibial base 1404 by a set screw 1414 or other fastener. The torsion spring load transferring device has the advantages of a long stroke and a compact, low profile footprint.

Figure 21:
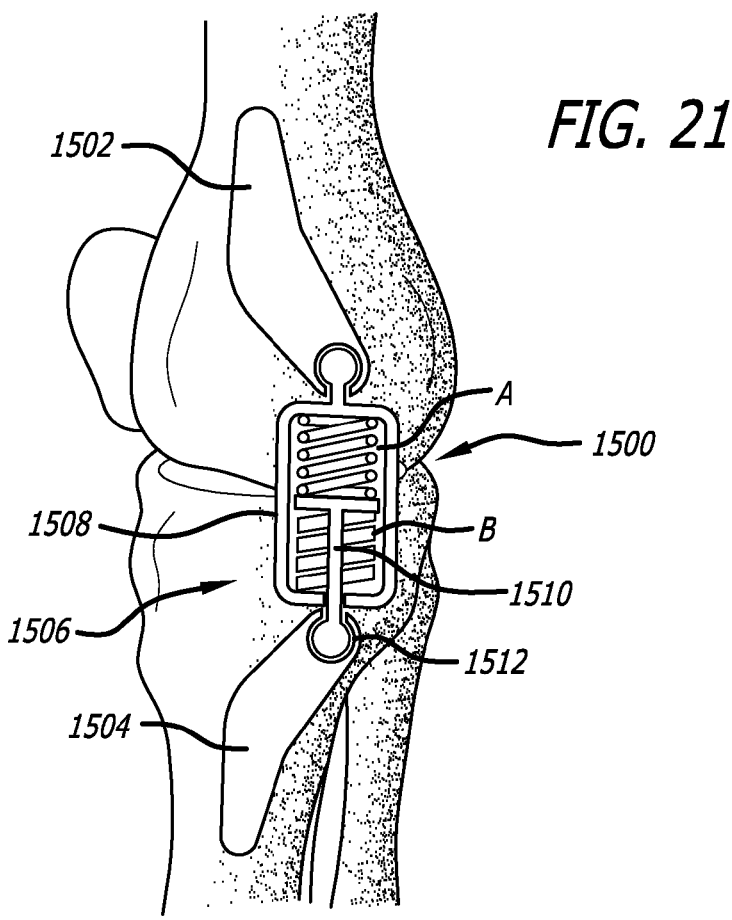
FIG. 21 is a perspective view of a load transferring system having tension and compression springs.

FIG. 21 schematically illustrates a load transferring device 1500 which includes a femoral base 1502, a tibial base 1504, and a spring element 1506 configured for implantation and coupling to a medial aspect of the knee joint. The spring element 1506 uses a tension spring A and a compression spring B to achieve a stroke of the spring element 1506 of about 1-2.5 inches. The spring element 1506 includes a main body 1508, which may be a substantially cylindrical enclosed body containing the two springs A and B and a piston 1510. The piston 1510 is connected to the tibial base 1504 by a ball and socket joint 1512, but could also be attached to the femoral base 1502 by a ball and socket joint or other articulating joint. The tension spring A is positioned between the piston 1510 and the upper end of the main body 1508 and is secured at each end acts in tension when the spring element 1506 is extended. The compression spring B is positioned around the piston 1510 and acts in compression as the spring element is extended. The two springs A and B act in combination provide a long stroke and can be used to tailor the forces unload the medial compartment of the joint different amounts at different flexion angles.

Figure 22:
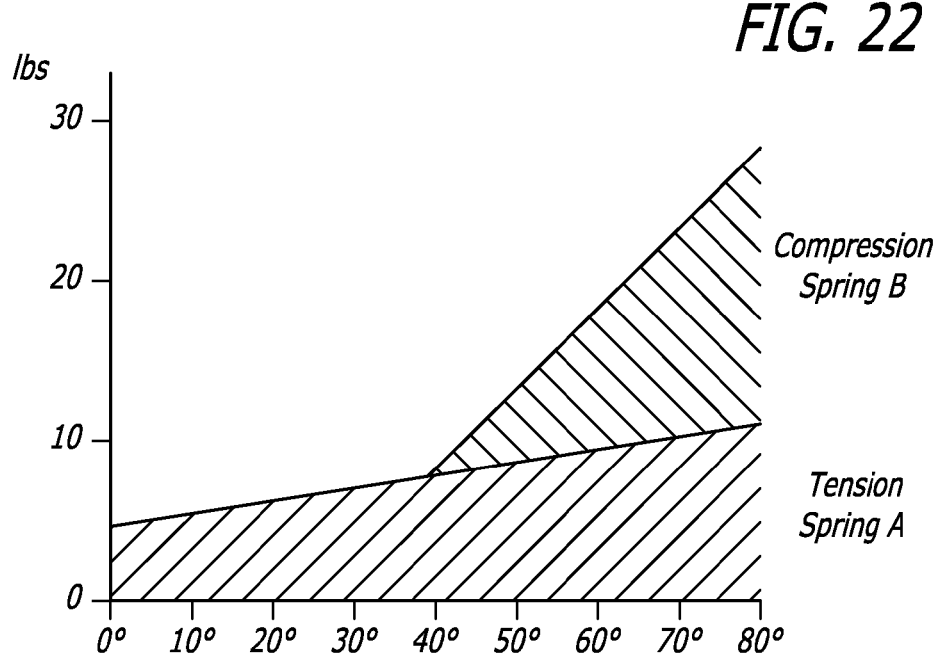
FIG. 22 is a graph of the load versus flexion angle for the system of FIG. 21.

One graph showing an example of a load transferring device 1500 having a tension spring A with a long stroke and a low spring force combined with a compression spring B with a high spring force and a shorter stroke results in the tensioning force shown in FIG. 22. The unloading a stance or extension of the knee joint is provided by the tension spring A in an amount of about 5 lbs, this tension increases to about 10 lbs at 80 degrees of flexion. Meanwhile, the compression spring B provides no force at extension and begins to provide a tension force at about 40 degrees flexion increasing to about 20 lbs of tension at 80 degrees flexion. The combine tension force of the load transferring device reaches a maximum of about 30 lbs. However, this maximum can be adjusted by changing the selected springs to achieve maximum tension any desired flexion angle. The graph of FIG. 22 is just one example of the combination of two springs to create a specific pattern of tensioning throughout flexion of the knee joint to accommodate patients having differing needs for unloading patterns.

The load transferring system may further comprise a first connector comprising a first articulating member, a first stationary member about which the first articulating member is configured to articulate, and a first fastener. Further, the load transferring system may include a second connector comprising a second articulating member, a second stationary member about which the second articulating member is configured to articulate, and a second fastener. In this regard, connecting the spring to the femoral base and the tibial base at operation 616 may comprise engaging the femoral base and the spring with the first connector and engaging the tibial base and the spring with the second connector at operation 618.

The load transferring systems described herein can be used permanently or temporarily. For temporary use, the use of unloading technology for a period of 3-6 months has been found to provide lasting pain relief possibly due to regeneration of cartilage in the joint. The load transferring systems can also be used adjunctively with various surgical techniques which may be performed on the lateral knee cartilage including but not limited to microfracture, cartilage repair, allograft, autograft, implantation of biologic, stem cell therapy. The load transferring systems are usable prophylactically in situations where there is a lateral meniscal injury. Osteoarthritis progression tends to be very rapid and progressive following meniscal injury and the device may be implanted shortly after the injury to prevent progression of the disease or prevent to onset of the disease entirely.

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope or spirit of the disclosure. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A load transferring system for a knee joint, the system comprising:
    a femoral base configured for implantation and coupling to a medial aspect of a femur;
    a tibial base configured for implantation and coupling to a medial aspect of a tibia; and
    a force applier element configured to be connected to the femoral base and the tibial base and configured to exert a tensile force between the femoral base and the tibial base during flexion of the knee joint so as to unload a lateral compartment of the knee joint by transferring load from the lateral compartment of the knee joint to a medial compartment of the knee joint;
    wherein, when the system is mounted to a medial aspect of a knee joint, the force applier applies 2.5 to 50 pounds of tension force between 10 to 90 degrees of flexion of the knee joint and applies less than 2 pounds of tension force when the knee joint is at zero degrees of flexion.

2. The load transferring system of claim 1, further comprising:
    a first connector configured to engage the femoral base and the force applier element; and
    a second connector configured to engage the tibial base and the force applier element.

3. The load transferring system of claim 2, wherein:
    the first connector comprises a first articulating member and a first stationary member about which the first articulating member is configured to articulate; and
    the second connector comprises a second articulating member and a second stationary member about which the second articulating member is configured to articulate.

4. The load transferring system of claim 3, wherein the first connector further comprises a first fastener configured to fasten the first stationary member to the femoral base, and wherein the second connector further comprises a second fastener configured to fasten the second stationary member to the tibial base.

5. The load transferring system of claim 3, further comprising:
    a piston coupled to one of the first articulating member and the second articulating member; and
    a cylinder coupled to the other of the first articulating member and the second articulating member and configured to receive the piston therein and allow for longitudinal movement therebetween.

6. The load transferring system of claim 5, wherein the piston and the cylinder are further configured to allow for rotational movement therebetween.

7. The load transferring system of claim 3, wherein the first articulating member and the second articulating member each define a channel configured to receive the force applier element.

8. The load transferring system of claim 7, wherein the force applier element comprises one of an elastomeric band, a polymer strip, a torsion spring, or a polymer body.

9. The load transferring system of claim 1, wherein the force applier element is configured to substantially avoid exerting the tensile force on the knee joint when the knee joint is in a fully extended position.

10. The load transferring system of claim 9, wherein the force applier element is configured to substantially avoid transferring a force between the femoral base and the tibial base under compression.

11. A load transferring system for a knee joint, the system comprising:
    a femoral base configured for implantation and coupling to a medial aspect of a femur;
    a tibial base configured for implantation and coupling to a medial aspect of a tibia; and a tension means configured to be connected to the femoral base and the tibial base, the tension means for exerting a tensile force between the femoral base and the tibial base during flexion of the knee joint so as to unload a lateral compartment of the knee joint by transferring load from the lateral compartment of the knee joint to a medial compartment of the knee joint;

wherein, when the system is mounted to a medial aspect of a knee joint, the tension means applies 2.5 to 50 pounds of tension force between 10 to 90 degrees of flexion of the knee joint and applies less than 2 pounds of tension force when the knee joint is at zero degrees of flexion.

12. The load transferring system of claim 11, further comprising:

a first connector means configured to engage the femoral base and the tension means; and a second connector means configured to engage the tibial base and the tension means.

13. The load transferring system of claim 12, wherein:

the first connector means comprises a first articulating member and a first stationary member about which the first articulating member is configured to articulate; and the second connector means comprises a second articulating member and a second stationary member about which the second articulating member is configured to articulate.

14. The load transferring system of claim 13, wherein the first connector means further comprises a first fastener means configured to fasten the first stationary member to the femoral base, and wherein the second connector means further comprises a second fastener means configured to fasten the second stationary member to the tibial base.

15. The load transferring system of claim 13, further comprising:

a piston coupled to one of the first articulating member and the second articulating member; and a cylinder coupled to the other of the first articulating member and the second articulating member and configured to receive the piston therein and allow for longitudinal movement therebetween.

16. The load transferring system of claim 15, wherein the piston and the cylinder are further configured to allow for rotational movement therebetween.

17. The load transferring system of claim 13, wherein the first articulating member and the second articulating member each define a channel configured to receive the tension means.

18. The load transferring system of claim 17, wherein the tension means comprises an elastomeric band.

19. The load transferring system of claim 11, wherein the tension means is configured to substantially avoid exerting the tensile force on the knee joint when the knee joint is in a fully extended position.

20. The load transferring system of claim 19, wherein the tension means is configured to substantially avoid transferring a force between the femoral base and the tibial base under compression.

21. The load transferring system of claim 1, wherein the force applier comprises a spring.

22. The load transferring system of claim 11, wherein the tension means comprises a spring.

* * * * *